US010779926B2

(12) United States Patent
Elahi

(10) Patent No.: US 10,779,926 B2
(45) Date of Patent: Sep. 22, 2020

(54) ADJUSTABLE FACIAL IMPLANT DEVICE

(71) Applicant: Ebrahim Elahi, New York, NY (US)

(72) Inventor: Ebrahim Elahi, New York, NY (US)

(*) Notice: Subject to any disclaimer, the term of this patent is extended or adjusted under 35 U.S.C. 154(b) by 86 days.

(21) Appl. No.: 16/180,815

(22) Filed: Nov. 5, 2018

(65) Prior Publication Data
US 2019/0133740 A1 May 9, 2019

Related U.S. Application Data

(60) Provisional application No. 62/582,211, filed on Nov. 6, 2017.

(51) Int. Cl.
*A61F 2/00* (2006.01)

(52) U.S. Cl.
CPC .... *A61F 2/0059* (2013.01); *A61F 2220/0008* (2013.01); *A61F 2220/0016* (2013.01); *A61F 2250/0003* (2013.01); *A61F 2250/0004* (2013.01)

(58) Field of Classification Search
CPC ........ A61F 2/28; A61F 2/2803; A61F 2/2875; A61F 2/3099; A61F 2/0059
See application file for complete search history.

(56) References Cited

U.S. PATENT DOCUMENTS

| | | | |
|---|---|---|---|
| 2007/0067041 A1* | 3/2007 | Kotoske | A61F 2/0059 623/17.18 |
| 2010/0249946 A1* | 9/2010 | Lesh | A61F 2/0059 623/23.72 |
| 2015/0209147 A1* | 7/2015 | Jordan | A61F 2/2875 623/17.18 |

* cited by examiner

*Primary Examiner* — Jason-Dennis N Stewart

(57) ABSTRACT

A facial implant device includes a support structure adapted to be coupled to a bone surface within a facial region, an outer structure adapted to contour to a predefined anatomy associated with the facial region, and an intermediary bladder structure located between the support structure and the outer structure. The intermediary bladder structure includes an internal volume that is adjusted in response to adapting the outer structure to contour to the predefined anatomy associated with the facial region.

8 Claims, 3 Drawing Sheets

ADJUSTABLE FACIAL IMPLANT DEVICE

BACKGROUND

The present invention generally relates to medical devices, and particularly to surgical implants used in facial reconstruction.

Facial reconstruction (e.g., associated with a patient's entire head, including the face and skull) often requires the surgical insertion of implant devices in order to not only correct post-traumatic deformities (e.g., car accidents, etc.) and disease related (e.g., cancer, etc.) defects, but also address the cosmetic concerns associated with enhancing or restoring facial appearance.

BRIEF SUMMARY

According to at least one exemplary embodiment, the adjustable facial implant, among other things, includes a construction that allows the implantation of a device to restore or enhance facial appearance.

According to at least one exemplary embodiment, a facial implant device can include a support structure adapted to be coupled to a bone surface within a facial region, an outer structure adapted to contour to a predefined anatomy associated with the facial region, and an intermediary bladder structure located between the support structure and the outer structure. The intermediary bladder structure includes an internal volume that is adjusted in response to adapting the outer structure to contour to the predefined anatomy associated with the facial region.

BRIEF DESCRIPTION OF THE SEVERAL VIEWS OF THE DRAWINGS

The drawings are not necessarily to scale. The drawings are merely schematic representations, not intended to portray specific parameters of the invention. The drawings are intended to depict only typical embodiments of the invention. In the drawings, like numbering represents like elements.

DETAILED DESCRIPTION

According to at least one exemplary embodiment, the adjustable facial implant, among other things, can be postoperatively shape corrected to address deformities or aesthetic deficiencies corresponding to the application of the implant device.

Figure 1A:
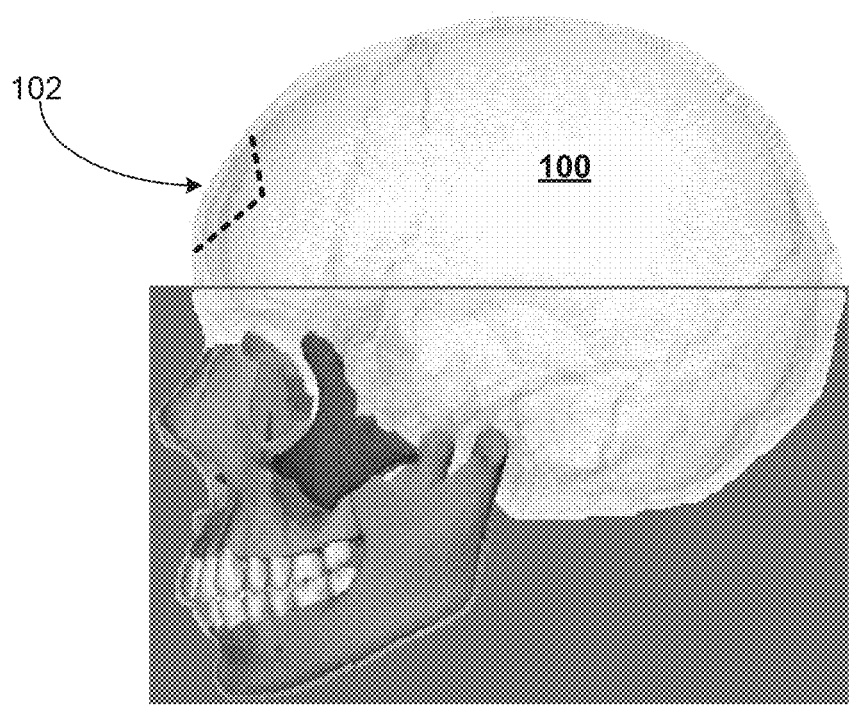
FIG. 1A illustrates an example of a defect requiring the application of an implant, according to one embodiment.
Figure 1B:
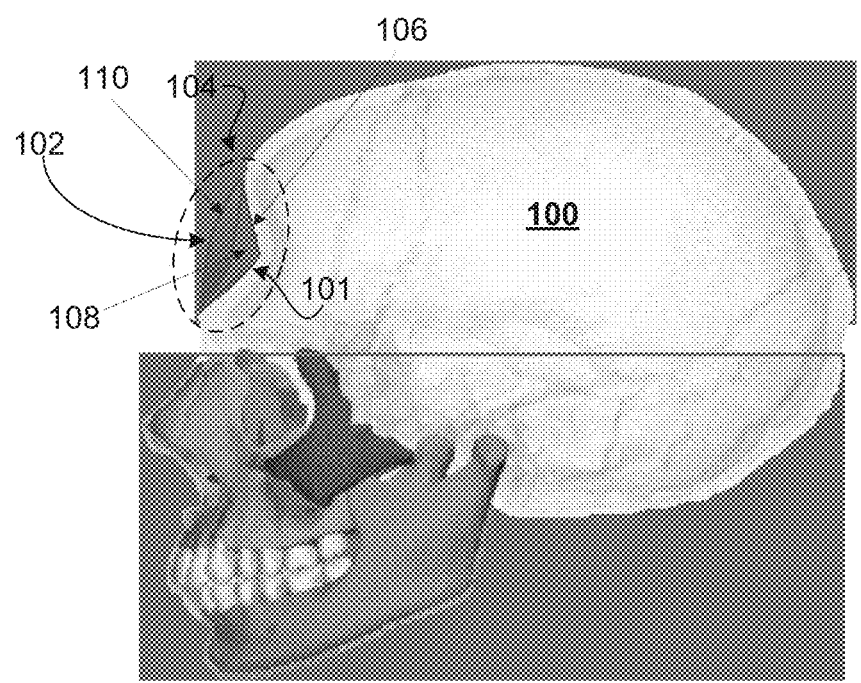
FIG. 1B illustrates an example of an adjustable facial implant that is applied to the defect shown in FIG. 1A, according to one embodiment.

Referring to FIG. 1A, for example, due to trauma, an area 102 of a patient's skull 100 can require a surgical repair to restore function and/or appearance. Accordingly, as depicted in FIG. 1B, an adjustable facial implant 104 may be applied to the involved region 102. The adjustable facial implant 104 includes a support structure 106, which can be prefabricated based on the anatomical location, or 3D printed for an individual patient. The support structure 106 may include an integrative material that would stabilize on the bone surface over time (e.g. porous polyethylene), and may further require a fixation (e.g., to a skeletal base 101) such as titanium alloy screws, absorbable screws, or any other suitable clipping/anchoring mechanism for coupling the support structure 106 to a skeletal base 101.

The adjustable facial implant 104 further includes an outer shell 110 and intermediary bladder structure 108 located between the support structure 106 and the outer shell 110. The outer shell 110 may be constructed from a soft material, such as silicone, in order to maximize desirable surface contour, minimize internal centrifugal pressure on soft tissues, minimize the destabilization of the implant 104, and/or mitigate tissue atrophy. The outer shell 110 should contour to the appropriate expected anatomy of the facial component. However, in some instances, postoperative correction to the overall shape and projection of this shell 110 is required to facilitate the above-mentioned contouring. This is achieved using the intermediate bladder structure 108, whereby the bladder size can be adjusted by filling the internal volume of the bladder 108 with a liquid or gel material. The intermediate bladder 108 may be contiguous and of the same material as the outer shell 110 or be entirely a separate structure and of a different material.

The intermediary bladder structure 108 located between the support structure 106 and the outer shell 110 can be expanded postoperatively with liquid (saline) or gel. As explained in further detail below, the intermediary bladder structure 108 can also include multiple separable zones to accommodate asymmetric volumetric requirements for fine tuning the shape of the implant to the desired contour of the patient's features. At the shell-bladder interface one or more ports with self-sealing valves can be provided for the filling and removal of tissue via a transcutaneous injection in the postoperative period. The entire shell/bladder interface may also be made of a material that allows for spontaneous sealing to occur upon injection with a needle. This would obviate the need for a specific port and valve mechanism.

Figure 2:
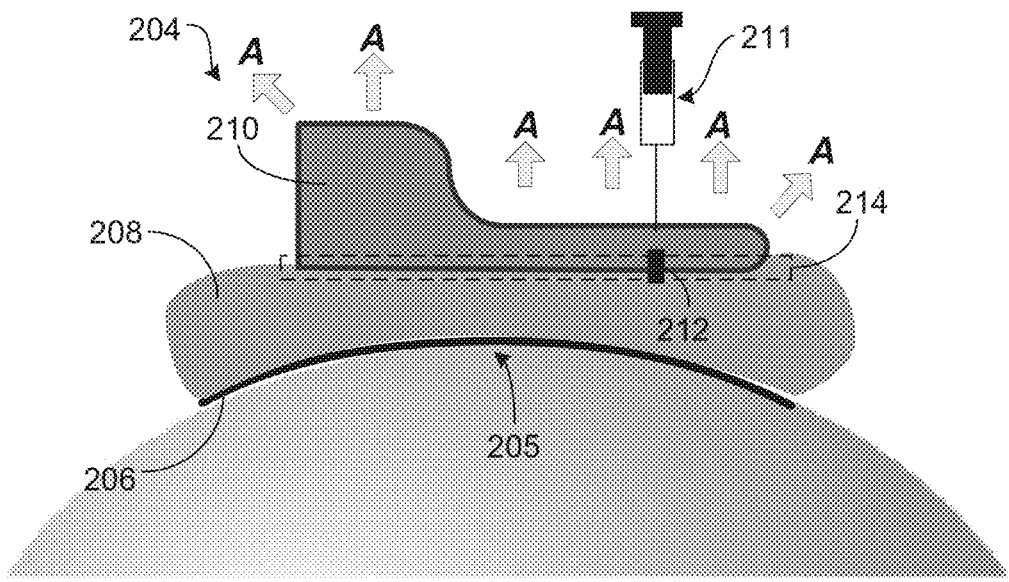
FIG. 2 illustrates a cross sectional view of an adjustable facial implant, according to one embodiment.

FIG. 2 illustrates a cross sectional view of an adjustable facial implant 204, according to one embodiment. The adjustable facial implant 204 includes a support structure 206 that may have an integrative material that stabilizes on the bone surface 205 over time (e.g. porous polyethylene), and may further require a fixation such as titanium alloy screws, absorbable screws, or any other suitable clipping/anchoring mechanism for coupling the support structure 206 to the bone surface 205.

The adjustable facial implant 204 further includes an outer shell 210 and an intermediary bladder structure 208 located between the support structure 206 and the outer shell 210. The outer shell 210 may be constructed from a soft material, such as silicone, in order to maximize desirable surface contour, minimize internal centrifugal pressure on soft tissues, minimize the destabilization of the implant 204, and/or mitigate tissue atrophy. The outer shell 210 should contour to the appropriate expected anatomy of the facial component. However, in some instances, postoperative correction to the overall shape and projection of this shell 210 is required to facilitate the above-mentioned contouring. This is achieved using the intermediate bladder structure 208, whereby the bladder size can be adjusted by filling the internal volume of the bladder 208 with a liquid or gel material. As depicted, the application of the liquid or gel may be facilitated via a valve device 212 located at an interface region 214 located between the intermediary bladder structure 208 and the outer shell 210. As the liquid or gel delivered by, for example, a syringe 211, fills the bladder 208, the outer shell's 210 geometric dimensions increase, as indicated by directional arrows A. Accordingly, the amount of dimensional expansion of the outer shell 210 may be determined by the volume of liquid or gel delivered within the bladder structure 208.

Figure 3:
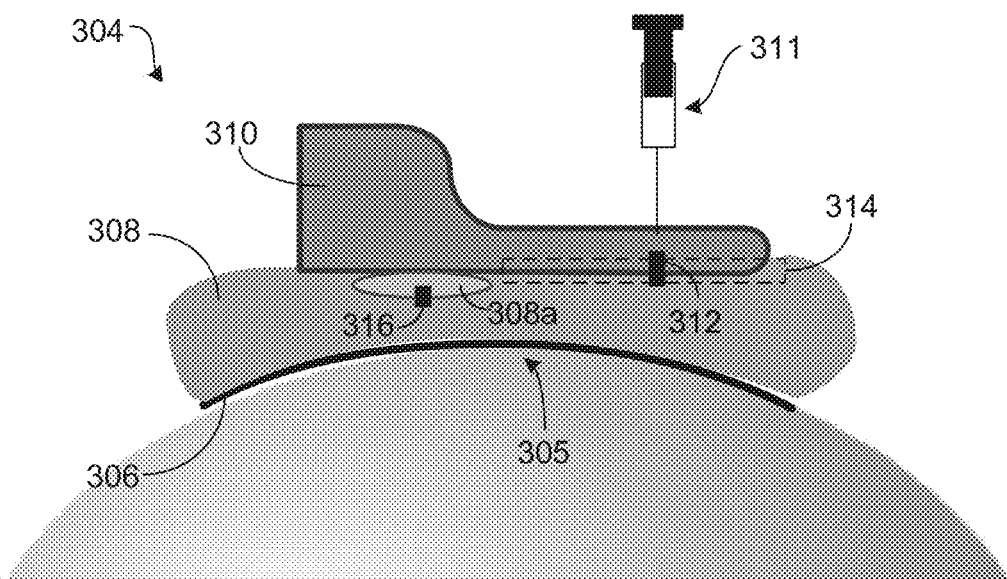
FIG. 3 illustrates a cross sectional view of an adjustable facial implant, according to another embodiment.

FIG. 3 illustrates a cross sectional view of an adjustable facial implant 304, according to another embodiment. The adjustable facial implant 304 includes a support structure 306 that may have an integrative material that stabilizes on the bone surface 305 over time (e.g. porous polyethylene), and may further require a fixation such as titanium alloy screws, absorbable screws, or any other suitable clipping/anchoring mechanism for coupling the support structure 306 to the bone surface 305.

The adjustable facial implant 304 further includes an outer shell 310 and an intermediary bladder structure 308 located between the support structure 206 and the outer shell 210. The outer shell 310 may be constructed from a soft material, such as silicone, in order to maximize desirable surface contour, minimize internal centrifugal pressure on soft tissues, minimize the destabilization of the implant 204, and/or mitigate tissue atrophy. The outer shell 310 should contour to the appropriate expected anatomy of the facial component. However, in some instances, postoperative correction to the overall shape and projection of this shell 310 is required to facilitate the above-mentioned contouring. This is achieved using the intermediate bladder structure 308, whereby the bladder size can be adjusted by filling the internal volume of the bladder 308 with a liquid or gel material. In this alternative embodiment, at least one other secondary bladder 308a is embedded within bladder 308, whereby the secondary 308a bladder is pressure activated and inflated via value device 316.

As depicted, the application of the liquid or gel may be facilitated via a valve device 312 located at an interface region 314 located between the intermediary bladder structure 308 and the outer shell 310. As the liquid or gel delivered by, for example, a syringe 311, fills the bladder 308, the outer shell's 310 geometric dimensions increase. In this embodiment, when the internal pressure of the bladder structure 308 reaches a threshold pressure value that activates valve device 316, the delivered gel or liquid flowing into bladder structure 308 starts to fill and inflate the secondary bladder 308a via valve 316. As the secondary bladder 308a inflates, the overall dimensional expansion of implant 304 increases in an asymmetrical manner since the secondary bladder 308a starts to inflate at a higher rate than the surrounding bladder structure 308.

Figure 4:
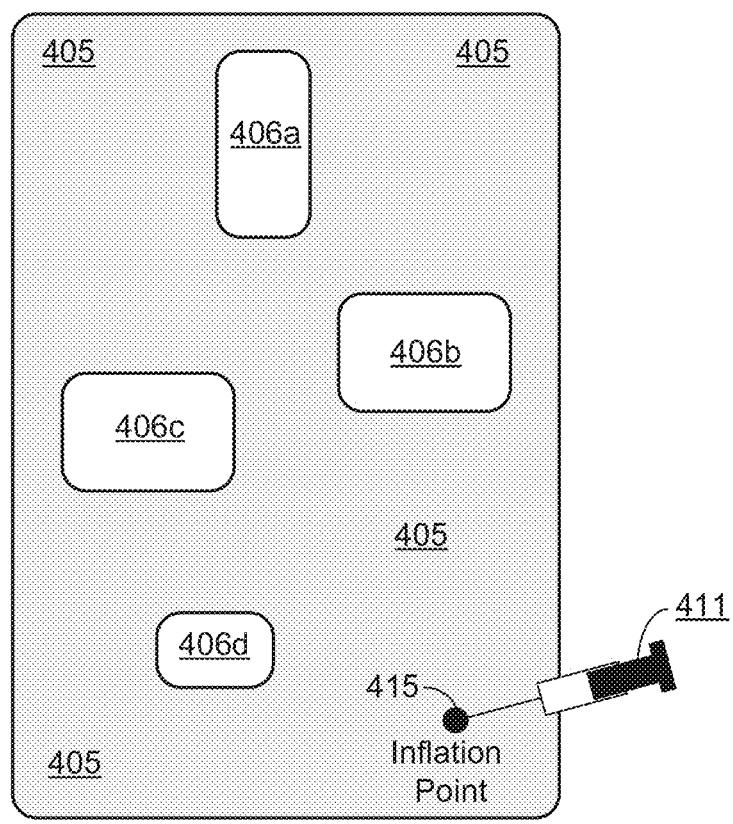
FIG. 4 illustrates a plan view of an example inflatable bladder structure corresponding to an adjustable facial implant similar to, or the same as, the embodiment depicted in FIG. 3, according to one embodiment.

FIG. 4 illustrates a plan view of an example inflatable bladder structure 405 corresponding to an adjustable facial implant similar to, or the same as, the embodiment depicted in FIG. 3, according to one embodiment. In the illustrated example, multiple secondary bladder structures 406a-406d can be embedded within the bladder structure 405 in the same or similar manner to that depicted and described in relation to FIG. 3. As the bladder structure 405 expands, the different secondary bladder structures 406a-406d can inflate based on their respective valves being activated at different pressure values. For example, secondary bladder structure 406d includes a smaller volume relative to the other secondary bladder structures 406a-406c. As such, secondary bladder structure 406d will start to inflate prior to the other secondary bladder structures 406a-406c. Secondary bladder structure 406a includes a smaller volume relative to secondary bladder structures 406b and 406c. As such, secondary bladder structure 406a will start to inflate after bladder 406d and prior to secondary bladder structures 406b-406c. Finally, following the activation of bladders 406a and 406d, the inflation of bladder structures 406b-406c will commence as the bladder 405 continues to be filled by the syringe 411 via the inflation valve 415. Thus, by adding more secondary bladder structures distributed and embedded within a main bladder structure, more asymmetrical control over the postoperative shape of the implant can be exhibited.

In the above described embodiments, where applicable, the intermediate bladder (e.g., 208, 308) may be contiguous and of the same material as the outer shell (e.g., 210, 310) or be entirely a separate structure and of a different material.

As such, based on the above features, the adjustable facial implant provides a postoperative shape correction mechanism to address certain unnatural visual effect corresponding to the application of the implant device.

What is claimed is:

1. A facial implant device, comprising:
   a support structure adapted to be coupled to a bone surface within a facial region;
   an outer structure adapted to contour to a predefined anatomy associated with the facial region;
   an intermediary bladder structure located between the support structure and the outer structure, the intermediary bladder structure having an internal volume that is adjusted in response to adapting the outer structure to contour to the predefined anatomy associated with the facial region, wherein the internal volume of the intermediary bladder structure includes a fill material that adjusts the intermediary bladder structure size in response to adapting the outer structure to contour to the predefined anatomy associated with the facial region; and
   a secondary bladder structure located within the intermediary bladder structure, wherein the secondary bladder structure inflates based on an internal pressure of the intermediary bladder structure reaching a first threshold pressure value in response to adjusting the intermediary bladder structure size with the fill material.

2. The implant device of claim 1, further comprising an anchoring mechanism for coupling the support structure to the bone surface.

3. The implant device of claim 1, wherein the support structure comprises an integrative material that stabilizes on the bone surface a finite over time.

4. The implant device of claim 3, wherein the integrative material comprises a porous polyethylene material.

5. The implant device of claim 1, wherein the fill material comprises a liquid or gel material.

6. The implant device of claim 1, further comprising a valve device located at an interface between the intermediary bladder structure and the outer structure, wherein the fill material is applied to the internal volume by injecting the fill material into the intermediary bladder structure using a syringe device.

7. A facial implant device, comprising:
   a support structure;
   an outer structure;
   an intermediary bladder structure located between the support structure and the outer structure, the intermediary bladder structure having an internal volume that is adjusted in response to adapting the outer structure to contour to a predefined anatomy associated with a facial region, wherein the internal volume of the intermediary bladder structure includes a fill material that adjusts the intermediary bladder structure size in response to adapting the outer structure to contour to the predefined anatomy associated with the facial region;

a secondary bladder structure located within the intermediary bladder structure, wherein the secondary bladder structure inflates based on an internal pressure of the intermediary bladder structure reaching a first threshold pressure value in response to adjusting the intermediary bladder structure size with the fill material; and an other secondary bladder structure located within the intermediary bladder structure that inflates based on an internal pressure of the intermediary bladder structure reaching a second threshold pressure value in response to adjusting the intermediary bladder structure size with the fill material, wherein the secondary bladder structure inflates prior to the other secondary bladder structure based on the secondary bladder structure having a smaller volume relative to the other secondary bladder structure.

8. The implant of device 1, wherein the outer structure comprises a silicon material.

\* \* \* \* \*